United States Patent [19]

Löhndorf et al.

[11] Patent Number: 5,429,010
[45] Date of Patent: Jul. 4, 1995

[54] APPARATUS FOR EXCHANGING MEASURING AND/OR SAMPLE PROBES

[75] Inventors: Wolfgang Löhndorf, Kempen; Hans-Wilhelm Schöck, Duisburg, both of Germany

[73] Assignee: Mannesmann Aktiengesellschaft, Dusseldorf, Germany

[21] Appl. No.: 191,454

[22] Filed: Feb. 3, 1994

[30] Foreign Application Priority Data

Feb. 24, 1993 [DE] Germany .............. 43 06 332.2

[51] Int. Cl.[6] .................. G01N 1/12; G01N 37/00
[52] U.S. Cl. .................. 73/866.5; 73/864.31; 73/DIG. 9
[58] Field of Sea ..... 73/866.5, 863.85, DIG. 9, 73/864.31, 863.82

[56] References Cited

U.S. PATENT DOCUMENTS 4,239,189 12/1980 Scherff ................. 73/DIG. 9 X
4,258,571 3/1981 Jürgens et al. ............ 73/DIG. 9 X
4,538,794 9/1985 Scherff .................. 73/DIG. 9 X

FOREIGN PATENT DOCUMENTS 0092636 10/1986 European Pat. Off. ....... C21C 5/46

*Primary Examiner*—Thomas P. Noland
*Attorney, Agent, or Firm*—Cohen, Pontani, Lieberman, Pavane

[57] ABSTRACT

An apparatus for exchanging measuring and/or sample probes which can be removed from a probe cartridge and then attached to a contact tube arranged at the lower end of a sublance. To enable a quick exchange of probes a gripper is provided for grasping the probe. The gripper is connected via a joint with an extension arm which is displaceable telescopically by a drive unit arranged so as to be movable on a rotatable and vertically adjustable table by at least two piston/cylinder units. A control device is provided for controlling the apparatus.

8 Claims, 3 Drawing Sheets

(B)

APPARATUS FOR EXCHANGING MEASURING AND/OR SAMPLE PROBES

BACKGROUND OF THE INVENTION

1. Field of the Invention

The present invention is directed to an apparatus for exchanging measuring and/or assaying or sample probes which can be removed from a probe cartridge and then attached to a contact tube arranged at the lower end of a sublance.

2. Description of the Prior Art

The use of devices for automatically fitting measuring lances with special measuring probes is already known.

For example, the European Patent EP-PS-0.092.636 describes a process and apparatus for handling measuring or sample probes in metal production in which the probe tube is removed horizontally from a probe cartridge, fastened vertically to a measuring lance, lowered into the metal bath, and then lifted out and disposed of.

For this purpose, the probe tube is removed from the probe cartridge by means of a cross-conveying device and is conveyed on a transporting device into the robot or manipulator. At this point, the probe tube is in a horizontal position. The manipulator is therefore swiveled into a vertical position after receiving the probe tube so that the probe tube is now situated precisely in the vertical measurement axis on which the measuring lance is fastened so as to be raised and lowered during operation.

A disadvantage in this process is that the multiple actions of transferring the probe tube from the probe cartridge to the manipulator and the subsequent swiveling of the probe tube in the vertical direction takes a relatively long period of time.

However, due to advances in process automation for the production of blown steel, the requirement for speed and accuracy in all components of the entire installation has increased progressively. The known devices can no longer meet these requirements.

SUMMARY OF THE INVENTION

Therefore, the object of the present invention is to develop a system which makes it possible to exchange probes quickly, e.g., for a repetition at the blowing end. Moreover, the system is so designed that existing installations can be converted without changing the existing system.

Pursuant to this object, and others which will become hereafter, one aspect of the present invention resides in an apparatus for exchanging measuring and/or sample probes which can be removed from a probe cartridge and then attached to a contact tube arranged at a lower end of a sublance, ill which apparatus a gripper is provided for grasping a probe. The gripper is connected with an extension arm by a joint. The extension arm is displaceable by means of a drive unit and in turn is arranged so as to be movable on a rotatable and vertically adjustable table by at least two piston/cylinder units. Furthermore, a control device is provided for controlling the overall apparatus.

In a further embodiment of the invention the joint permits rotating movement of the gripper in X, Y and Z directions. Furthermore, the joint can be a universal joint.

In another embodiment of the invention the extension arm is telescopically displaceable. In still another embodiment of the invention the drive unit is movably connected with the table in the region of its corners by four piston/cylinder units. Each of the piston/cylinder units being controlled separately by the control means.

Another embodiment of the invention provides that the table, the drive unit, the extension arm, the joint and the gripper are each controlled independently from one another by the control device.

In still a further embodiment of the invention the probe cartridge is provided with a number of probe ducts for accommodating the various probes.

According to the invention, the apparatus for exchanging measuring and/or sample probes is furnished with six degrees of freedom which makes it possible to drive around structures arranged about the room. Moreover, the apparatus is outfitted with drives that enable a total cycle time for exchanging probes within the desired short space of time.

This is accomplished advantageously by making use of the fact that the working processes from the time of the removal of the probes from the probe cartridge to the insertion of the swiveled probes into the measuring lances can be effected in one work step.

The various features of novelty which characterize the invention are pointed out with particularity in the claims annexed to and forming a part of the disclosure. For a better understanding of the invention, its operating advantages, and specific object is attained by its use, reference should be had to the drawing and descriptive matter in which there are illustrated and described preferred embodiments of the invention.

DETAILED DESCRIPTION OF THE PREFERRED EMBODIMENTS

Figure 1:
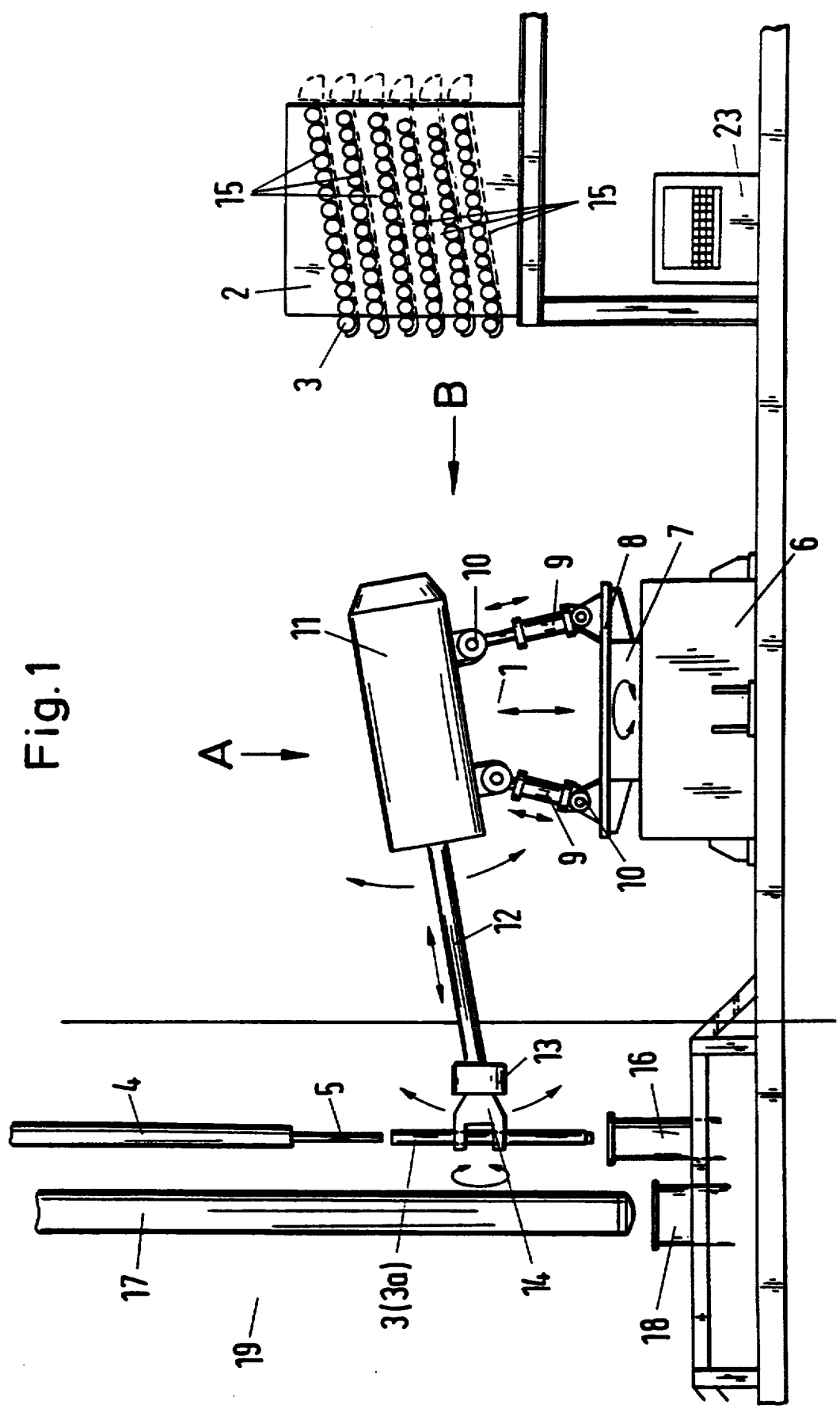
FIG. 1 shows a view of the area of use of an apparatus, according to the invention, with a waste gas boiler, a blowing lance, a blowing lance dome, a sublance and a sublance dome.
Figure 2:
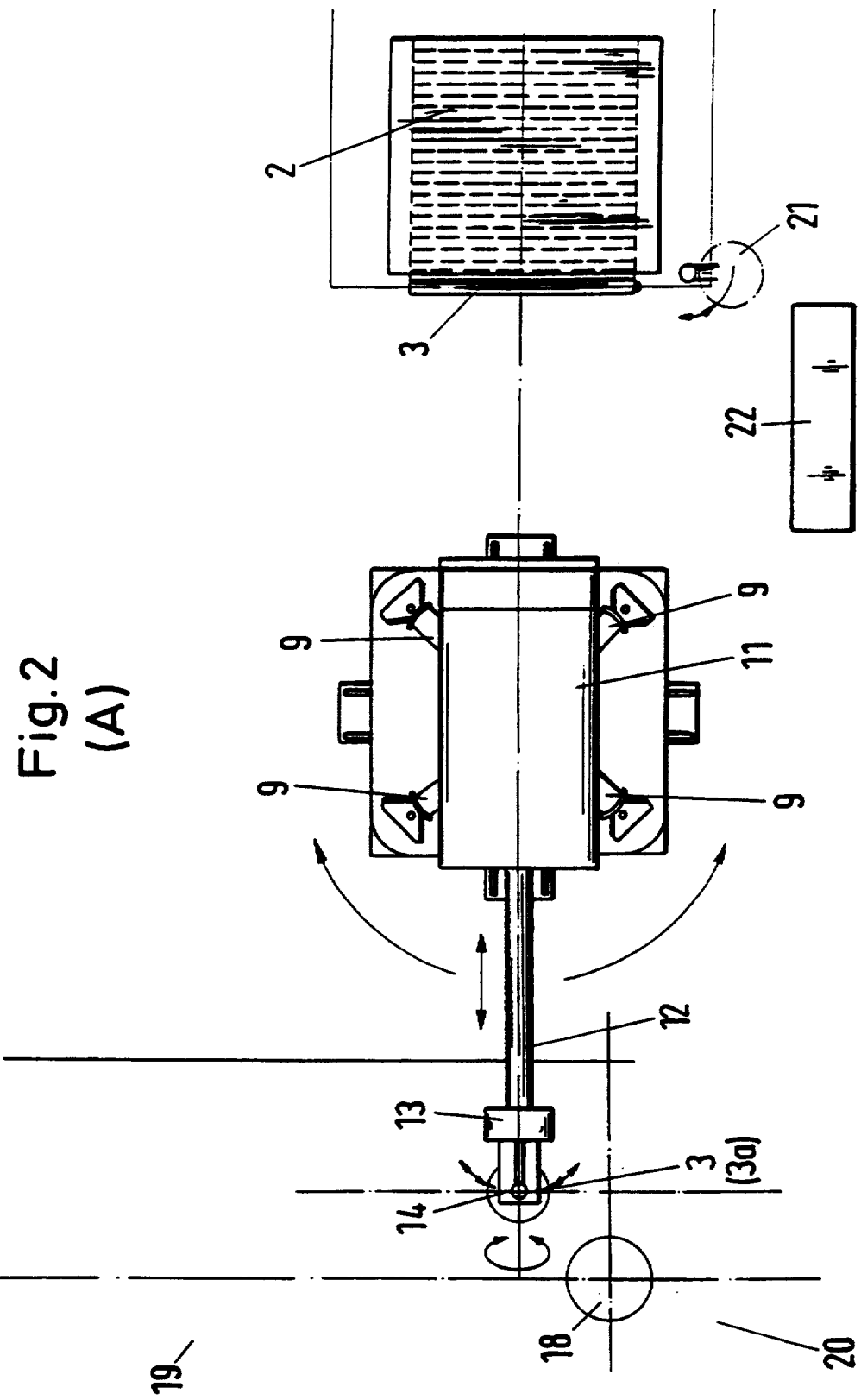
FIG. 2 shows a top view of FIG. 1.
Figure 3:
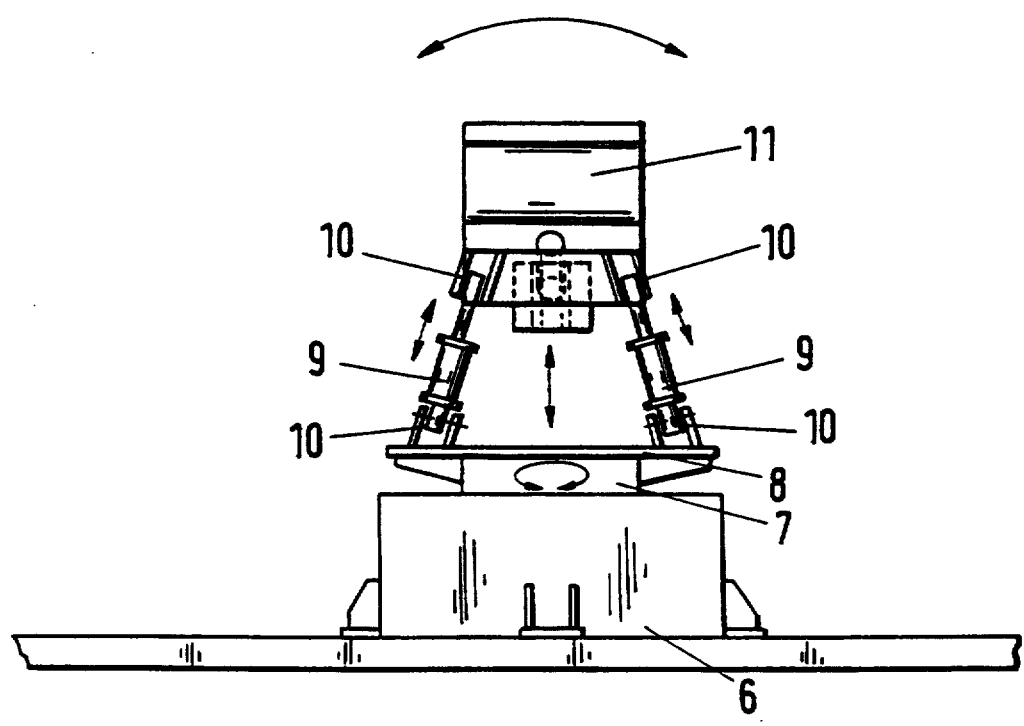
FIG. 3 shows a side view of FIG. 1.

According to FIGS. 1 to 3, the probes 3 required for a specific measurement are stored in the probe cartridge 2 in corresponding grooves or ducts 15.

When the command for a determined measurement is given from the control station, a placement program is started and the drives of the lifting and rotating unit 7, joint 13, and extension arm 12 are activated by the control unit 23 and the apparatus 1 moves toward the probe 3. The grippers 14 connected with the joint 13 are then closed.

The probe 3 is removed from the cartridge 2 in the horizontal position and brought into the vertical position by the combined or superposed movements of the piston/cylinder units 9, the drive unit 11 for telescoping of the extension arm 12, and the joint 13.

The lifting and rotating unit 7 then swivels while the extension arm 12 telescopes into the probe placement position at the same time. The bearings 10 of the piston/cylinder units 9 are designed to accommodate the swiveling movements caused by the reciprocating movement of the piston/cylinder units 9.

A crucial point in this respect is that the combination of the lifting and rotating unit 7, the drive unit 11 for telescoping the extension arm 12, and the joint 13 makes it possible to move toward or around all spatial points in the orbit of the exchanging apparatus. After reaching the placement position, the probe 3 can be placed on the contact tube 5 of the sublance 4 either by means of the lifting unit 7 or by means of the piston/cylinder units 9 accompanied by a simultaneous tilting of the joint 13.

In view of the fact that each of the piston/cylinder units 9, the revolving table 8, the drive unit 11, the extension arm 12, the joint 13, and the grippers 14 can be controlled independently from one another by the control device 23, the probes 3 can be attached to the contact tube reliably and correctly regardless of the alignment of the measuring lance 4.

When taking a simple temperature measurement, the spent or used probe 3a is withdrawn from the contact tube 5 of the sublance 4 after the measurement and is disposed of in the converter 20 through the sublance dome 16.

When temperature sample probes are employed, the used probe 3a is withdrawn from the contact tube 5 and brought by the apparatus I to the separating station 21, where the lower portion of the probe containing the sample chamber is separated from the probe and transported to the converter platform via a drop pipe. The rest of the probe is then either disposed of in the converter 20 through the sublance dome 16 or is thrown into a disposal station 22 provided for this purpose.

Due to the programmable control unit 23 of the apparatus 1, all spatial coordinates can be entered by means of the "teach in" procedure and then carried out in the real-time program. As a result of the centralization of all control commands in the control unit 23 of the apparatus 1, the susceptibility of previously known systems to disruption can be overcome to a great extent.

The invention is not limited by the embodiments described above which are presented as examples only but can be modified in various ways within the scope of protection defined by the appended patent claims.

We claim:

1. An apparatus for exchanging measuring and/or sample probes which call be removed from a probe cartridge and then attached to a contact tube arranged at a lower end of a sublance, comprising: a gripper for grasping a probe; all extension arm; a joint for connecting the gripper with the extension arm; drive means for displacing the extension arm; a rotatable and vertically adjustable table; at least two piston/cylinder units provided to movably connect the drive unit to the rotatable and vertically adjustable table; and control means for controlling the apparatus.

2. An apparatus according to claim 1, wherein the .joint allows a rotating movement of the gripper in X, Y and Z directions.

3. An apparatus according to claim 1, wherein the .joint is a universal joint.

4. An apparatus according to claim 1, wherein the extension arm is telescopically displaceable.

5. An apparatus according to claim 1, wherein the drive means is movably connected with the table in a region of its corners by four piston/cylinder units.

6. An apparatus according to claim 5, wherein each piston/cylinder unit call be controlled separately by the control means.

7. An apparatus according to claim 1, wherein the table, the drive means, the extension arm, the joint, and the gripper can be controlled independently from one another by the control means.

8. An apparatus according to claim 1, wherein the probe cartridge has a number of probe ducts for accommodating the probes.

* * * * *